United States Patent [19]

Bruner

[11] 4,185,638
[45] Jan. 29, 1980

[54] PRESSURE INDICATORS FOR INFLATABLE CUFF-TYPE CATHETERS

[75] Inventor: James D. Bruner, Englewood, Colo.

[73] Assignee: Sandoz, Inc., E. Hanover, N.J.

[21] Appl. No.: 758,309

[22] Filed: Jan. 10, 1977

Related U.S. Application Data

[62] Division of Ser. No. 591,601, Jun. 30, 1975, Pat. No. 4,016,885.

[51] Int. Cl.² ............... A61M 16/00; A61M 25/00
[52] U.S. Cl. ................. 128/349 B; 116/270; 116/DIG. 8; 128/207.15
[58] Field of Search ........ 128/349 B, 349 BV, 350 R, 128/350 V, 351, 348; 116/114 PV, DIG. 8, DIG. 9, 266, 270; 73/731

[56] References Cited

U.S. PATENT DOCUMENTS

| 2,883,986 | 4/1959 | DeLuca et al. | 128/351 |
| 3,407,817 | 10/1968 | Galleher, Jr. | 128/351 |
| 3,642,005 | 2/1972 | McGinnis | 128/351 |
| 3,810,474 | 5/1974 | Cross | 128/351 |
| 3,848,605 | 11/1974 | Harautuneian et al. | 128/351 |
| 3,911,904 | 10/1975 | Saba | 73/731 X |
| 4,016,885 | 4/1977 | Bruner | 128/349 B |

FOREIGN PATENT DOCUMENTS 485219 10/1929 Fed. Rep. of Germany ............ 128/341

Primary Examiner—Robert W. Michell
Assistant Examiner—Michael H. Thaler
Attorney, Agent, or Firm—Gerald D. Sharkin; Robert S. Honor; Walter F. Jewell

[57] ABSTRACT

Inflatable cuff-type catheters, e.g., endotracheal and tracheotomy tubes, with cuff pressure indicators are provided. One indicator comprises an expandable chamber with an open-ended spring about the mid-section of the chamber. As the chamber expands, the spring also expands to indicate the gas pressure in the cuff.

2 Claims, 7 Drawing Figures

PRESSURE INDICATORS FOR INFLATABLE CUFF-TYPE CATHETERS

This is a division of application Ser. No. 591,601 filed June 30, 1975, now U.S. Pat. No. 4,016,885.

This invention relates to inflatable cuff-type catheters. In one particular aspect, it relates to pressure indicator for inflatable cuff-type catheters.

Inflatable cuff-type catheters, e.g., endotracheal and tracheotomy tubes, are a common way of administering inhalant anesthetics to a patient during surgery or to mechanically ventilate a patient. A major problem in patients who must be intubated is that the tube cuff, which must be inflated to seal the trachea around the tube, is over inflated.

This causes damage to the surrounding tissues. This over inflation is caused because the most often used measurement of cuff inflation is volume. However, it is pressure which is the damage causing parameter in the modern, high residual volume cuffs.

It is, therefore, an object of this invention to provide an inline pressure indicator for endotracheal and tracheotomy tubes employing cuffs to prevent trauma to the trachea due to overpressurization.

This and other objects of the invention will become apparent from the following detailed description and drawings wherein.

Figure 1:
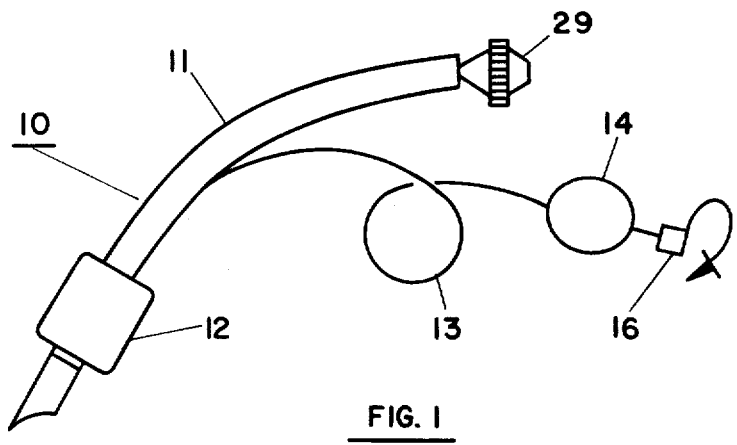
FIG. 1 is a side view of an inflatable cuff-type catheter of this invention.

Broadly, this invention provides an inflatable cuff-type catheter for insertion into a body passage and comprises a flexible tube having distal and proximal ends, at least one gas inflatable cuff encircling the flexible tube near the distal end with the cuff having its opposite ends sealed to the tube. A branched tube is provided, which is connected at an inner end to the interior of the cuff. An inflation means and a pressure indicator means, e.g., gauge, scale, and the like, are connected in series to the cuff through the outer end of the branched tube for access outside the body passage. The indicator means preferably comprises an expandable chamber having an open-ended spring wound about the mid-section of the chamber, which spring expands with the chamber to indicate by a pre-determined setting on the surface of the spring the gas pressure within the inflatable cuff.

Another indicator means comprises an expandable chamber having at one end a cone-shaped shell encircling the chamber. The apex end of the shell encircles and adheres to the branched tube. The chamber has indicia on the surface of the shell end, wherein the chamber upon expansion progressively exposes the indicia from beneath the shell to indicate by a pre-determined progression of the indicia the gas pressure within the inflatable cuff.

A still further indicator means comprises an expandable chamber having a substantially "V"-shaped longitudinal depression therein. There is also provided a top section, which may be substantially rectangular bridging the "V"-shaped depression at the circumference of the chamber and secured to the chamber on one side of the "V"-shaped depression. The chamber has indicia on the circumferal surface beneath the nonadhered portion of the top section, and upon expansion progressively exposes the indicia from beneath the top section to indicate, by a pre-determined progression of the indicia, the gas pressure within the inflatable cuff.

It is a feature of this invention that the expandable chamber encircles the branched tube and has opposite ends sealed thereto. However, it will be understood by those skilled in the art that it is not necessary to the function of the pressure indicator that the expandable chamber encircles the branched tube. For example, the chamber may be communication with the branched tube by means of a "T"-shaped fitting connected to the branched tube. When the expandable chamber encircles the branched tube, the branched tube may be provided with radial openings communicating with the interior of the chamber for the passage of the cuff inflating gas into the chamber. Optionally, the branched tube may be attached and sealed to the opposite ends of the expandable chamber, such that no portion of the branched tube passes through the chamber, but the portions of the branched tube at either end of the chamber communicate with the interior of the chamber.

In the practice of this invention, the inflatable cuff-type catheter is inserted into a body passage, e.g., trachea, and air is applied from the inflation means through the branched tube and into the inflation cuff to expand it. At the same time the air is entering the indicator means and expanding it simultaneously with the expansion of the inflatable cuff. Depending upon which of the above indicator means is employed, the expanding indicator means will indicate, by means of pre-selected settings, the pressure within the inflatable cuff.

Referring now to the drawing, there is shown in FIG. 1, generally at 10 an inflation cuff-type catheter of this invention. The catheter comprises a flexible tube 11, an inflatable cuff 12, a branched tube 13, a pressure indicator 14, and an inflation means 16.

Figure 2:
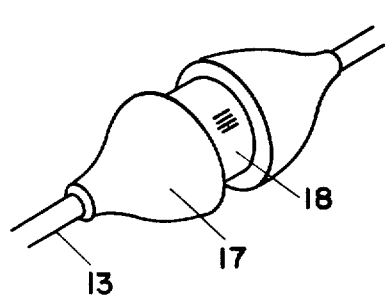
FIG. 2 is an isometric view of a pressure indicator of a catheter of this invention.
Figure 3:
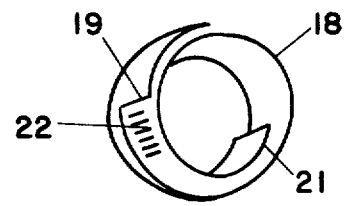
FIG. 3 is an isometric view of the spring mechanism of the pressure indicator of FIG. 2.

Referring to FIG. 2 and FIG. 3, there is shown a preferred pressure indicator of this invention. It comprises a branched tube 13, an inflatable chamber 17, and an open-ended spring 18. The spring 18 may be comprises of any suitable metallic material, which will expand upon the inflation of the chamber 17. The spring 18 preferably has a cut-out portion 19, beneath which a coil section 21 has indicia 22 imprinted thereon. As the spring expands, the cut-out portion 19 reveals progressively the indicia 22. This indicia may be in the form of a scale depicting pressure and is calibrated to show the pressure within the inflatable cuff 12.

Figure 4:
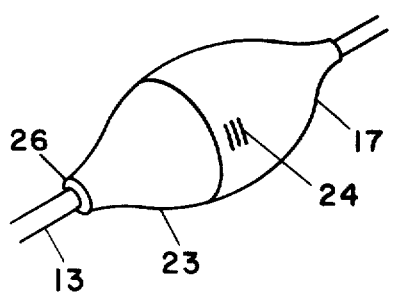
FIG. 4 is an isometric view of another pressure indicator of a catheter of this invention.

A second embodiment of the invention is shown in FIG. 4, wherein a cone-shaped shell 23 covers and encircles one end of the chamber 17. Upon the chamber 17 are indicia 24, which upon the expansion of the chamber 17 appear from beneath the shell 23. The progressive appearance of the indicia 24 is directly related to the pressure within the inflatable cuff 12 and may be scaled to read in terms of the pressure within cuff 12. The shell 23 may be affixed at its apex end 26 to the branched tube 13 by having the branched tube 13 pass through its apex.

Figure 5:
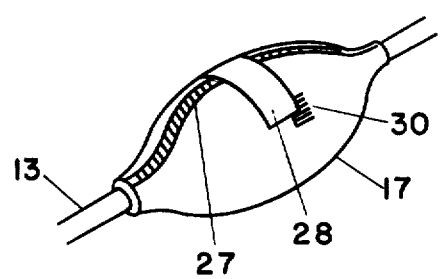
FIG. 5 is an isometric view of an additional pressure indicator of a catheter of this invention.

A third embodiment of this invention is depicted in FIG. 5, wherein the expandable chamber 17 has a "V"-shaped longitudinal depression 27. Across the circumference of the chamber 17 and branching over the depression 27, is a top section 28, which may be substantially rectangular in shape. The top section 28 is adhered to the chamber 17 on one side of the "V"-shaped depression 27 by any suitable prior art means, e.g., adhesive. Beneath the free-end of the top section 28, indicia 30 are marked upon the surface of the chamber 17. Upon the expansion of the chamber 17, the "V"-shaped groove 27 widens and in so doing progressively exposes the indicia beneath the top section 28. This indicia, as noted above, is calibrated to indicate the pressure within the cuff 12.

Figure 6:
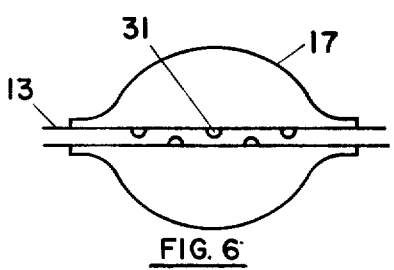
FIG. 6 is a side view of an expandable chamber of a pressure indicator of this invention.
Figure 7:
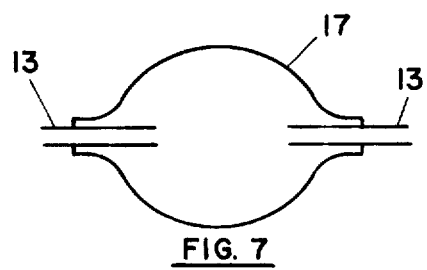
FIG. 7 is a side view also of an expandable chamber of a pressure indicator of this invention.

FIG. 6 and FIG. 7 illustrate two means by which the chamber 17 may be simultaneously inflated with the cuff 12. In FIG. 6, the branched tube 13 is provided with radial openings 31 in the portion of the tube 13 within the chamber 17. Air from the inflation means 16 passes through the openings 31 and inflates the chamber 17. In FIG. 7, the branched tube 13 does not pass through the chamber 17 but communicates with the chamber 17 at both ends of it. Air from the inflation means 16 enters the chamber 17, via one section of the branched tube 13, passes through the chamber 17 (inflating it) and passes, via the other section of the branched tube 13 from the chamber 17 to the cuff 12.

The catheter 10 may be fitted with a standard commercial inflating means 16, such as a Luer fitting for cuff inflation. The flexible tube 11 may also be fitted with various adaptors 29, e.g., 15 mm. adaptor, to which may be attached sources of air or anesthetic gases.

While the pressure indicator of this invention has been described in terms of the above pressure indicators, it is also within the scope of this invention to include other pressure indicating devices, such as gauges and the like, which may be connected in series with the inflatable cuff 12 and the inflation means 16; to indicate the pressure within the cuff 12.

What is claimed is:

1. An inflatable cuff-type catheter for insertion into a body passage comprising in combination a flexible tube having distal and proximal ends, at least one gas inflatable cuff encircling the flexible tube near the distal end and having opposite ends sealed thereto; a branched tube connected at an inner end to the interior of the cuff; and an inflation means and a pressure indicator means connected in series to the cuff through the outer end of the branch tube for access outside the body passage, the indicator means comprising an expandable chamber encircling the branched tube with opposite ends sealed thereto; the branched tube having radial openings communicating with the interior of the chamber for the passage of the cuff inflating gas into the chamber, the expandable chamber having at one end a cone-shaped shell encircling the chamber, the apex end of the shell encircling and adhered to the branched tube, the chamber having indicia on the surface of the shell end, wherein the chamber upon expansion is adapted to progessively expose the indicia and by a pre-determined progression of the indicia the gass pressure within the inflatable cuff.

2. An inflatable cuff-type catheter for insertion into a body passage comprising in combination a flexible tube having distal and proximal ends, at least one gas inflatable cuff encircling the flexible tube near the distal end and having opposite ends sealed thereto; a branched tube connected at an inner end to the interior of the cuff; and an inflation means and a pressure indicator means connected in series to the cuff through the outer end of the branch tube for access outside the body passage, the indicator means comprising an expandable chamber having opposite ends attached and sealed to the branched tube which communicates with the interior of the chamber, the expandable chamber having at one end a cone-shaped shell encircling the chamber, the apex end of the shell encircling and adhered to the branched tube, the chamber having indicia on the surface of the shell end, wherein the chamber upon expansion is adapted to progressively expose the indicia and by a pre-determined progression of the indicia the gas pressure within the inflatable cuff.

* * * * *